US008623300B2

(12) United States Patent
Williamson, IV (10) Patent No.: US 8,623,300 B2
(45) Date of Patent: Jan. 7, 2014

(54) BIOPSY SUPPORT WITH SECTIONABLE RESILIENT CELLULAR MATERIAL

(75) Inventor: Warren P. Williamson, IV, Loveland, OH (US)

(73) Assignee: Biopath Automation, L.L.C., Loveland, OH (US)

( * ) Notice: Subject to any disclaimer, the term of this patent is extended or adjusted under 35 U.S.C. 154(b) by 0 days.

(21) Appl. No.: 13/610,204

(22) Filed: Sep. 11, 2012

(65) Prior Publication Data

US 2013/0004990 A1 Jan. 3, 2013

Related U.S. Application Data

(62) Division of application No. 11/954,112, filed on Dec. 11, 2007, now Pat. No. 8,383,067.

(60) Provisional application No. 60/869,629, filed on Dec. 12, 2006.

(51) Int. Cl.
*A61B 10/00* (2006.01)
*B01L 3/00* (2006.01)

(52) U.S. Cl.
USPC ........... 422/536; 422/564; 436/174; 435/40.5

(58) Field of Classification Search
USPC ........... 422/536; 436/174; 206/1, 5, 485, 486; 435/40.5, 40.52, 288.3; 600/562, 564; 604/22; 83/167, 915.5
See application file for complete search history.

(56) References Cited

U.S. PATENT DOCUMENTS

| 5,629,014 | A | * | 5/1997 | Kwiatek et al. | 424/449 |
| 2005/0043816 | A1 | * | 2/2005 | Datta et al. | 623/23.61 |
| 2005/0100981 | A1 | * | 5/2005 | Bjørnsen | 435/40.5 |
| 2007/0116612 | A1 | * | 5/2007 | Williamson, IV | 422/102 |

FOREIGN PATENT DOCUMENTS

WO WO 0019897 A1 * 4/2000

OTHER PUBLICATIONS

Japanese Patent Office; Office Action in Japanese Patent Application No. 2009-541332 dated Nov. 6, 2012.

* cited by examiner

*Primary Examiner* — Dean Kwak
(74) *Attorney, Agent, or Firm* — Wood, Herron & Evans, L.L.P.

(57) ABSTRACT

A histologic tissue sample support device includes a tissue support formed of material that can be successfully sectioned in a microtome and is resistant to degradation from solvents and chemicals used to fix, process and stain tissue. A resilient cellular material is coupled to the tissue support and is configured to engage and retain tissue in place during processing and embedding. The resilient cellular material is also capable of successful sectioning in the microtome and porous to allow infiltration of the solvents and chemicals used to fix, process and stain tissue, and of embedding material used to embed the tissue while the tissue is retained by the resilient cellular material.

8 Claims, 8 Drawing Sheets

BIOPSY SUPPORT WITH SECTIONABLE RESILIENT CELLULAR MATERIAL

This application is a divisional of application Ser. No. 11/954,112, filed Dec. 11, 2007 (pending) which claims the benefit of U.S. Provisional Patent Application Ser. No. 60/869,629, filed Dec. 12, 2006 (expired), the disclosures of which are also fully incorporated by reference.

TECHNICAL FIELD

The present invention generally relates to supports for handling and embedding tissue samples for pathological analysis and, more particularly, to sectionable supports which can receive one or more tissue samples and be embedded and subsequently microtomed with the tissue sample or samples.

BACKGROUND

To accurately diagnose various tissue diseases and conditions, medical personnel must remove one or more samples of tissue from the body of a patient. This process of harvesting tissue from the body is known as a biopsy. Once the tissue sample or samples are removed and sent to a pathology laboratory, the tissue will go through a series of procedures performed by a histotechnician and, ultimately, a pathologist, in order to diagnose one or more conditions associated with the tissue. The present invention generally relates to those procedures that are normally performed by the histotechnician to prepare the tissue sample or samples into slides that may be analyzed under a microscope by the pathologist.

Although the singular term "sample" is used throughout this specification, it should be understood that this term likewise encompasses plural "samples" as well. Once a tissue sample is removed from the body of a patient, it is typically placed into a specimen container containing a tissue fixative solution and then the container is transported to a pathology laboratory. The tissue will undergo a process known as "grossing-in" in the pathology lab during which a histotechnician will retrieve the tissue sample from the container, typically cut the tissue into appropriate sizes for tissue processing, place individual samples into the appropriate sized small plastic tissue cassettes, and assign tracking numbers to each cassette. These tracking numbers are then logged into a tracking system used in the laboratory. For the smallest tissue samples, which may only be scrapings, the cassette includes fine mesh openings on the sides and bottoms. In other situations involving very small tissue samples, the samples are placed into a bag that resembles a tea bag that prevents the smallest tissue samples from escaping. Larger tissue samples are placed into cassettes having somewhat larger slotted openings which are nevertheless smaller than the tissue sample inside the cassette.

The cassettes are then placed into a stainless steel perforated basket and run through a tissue processing machine, often overnight. This machine uses a combination of vacuum, heat, and chemicals to remove the interstitial fluids within the tissue. Once the fluids have been removed from the tissue samples, the processing machine immerses the tissues samples in a bath of a hardenable material such as molten paraffin (i.e., a form of wax) so that the interstices in the tissue are replaced with paraffin. The histotechnician then removes the basket from the machine and removes the individual tissue cassettes. In a conventional procedure practiced for many years, the histotechnician individually removes the tissue sample from each cassette. The histotechnician must carefully orient the tissue sample, based on tissue type, into a stainless steel base mold that is roughly the size of the tissue cassette and is partially filled with molten paraffin. The tissue sample must be manually held, typically using forceps, against the bottom of the mold. If it is not, this could compromise the ability to make proper slices of the tissue sample later in a microtome. The molten paraffin is then rapidly cooled on a refrigerated plate, which may be a thermal electric cooler (TEC), to partially solidify the paraffin thereby holding the tissue sample in the proper orientation against the bottom of the mold. The cassette is then placed on top of the base mold and an embedding material, which is also typically paraffin wax, is poured through the opened top of the cassette into the base mold. The cassette changes its function at this point in the procedure from a tissue holding component to a fixture type device for mounting in the microtome and making shavings or slices from the solidified paraffin in the microtome. The base mold is chilled until all of the molten paraffin has hardened and the histotechnician removes the stainless steel base mold from the block of embedded paraffin. The tissue sample is thus embedded within a rectangular block of hard paraffin with a plastic tissue cassette on the opposite side. As mentioned, the cassette may then be used as a holder or fixture in the chuck of the microtome. As with the tissue processing machine, the embedding process is accomplished in a batch fashion during which an average histotechnician may embed approximately 40 to 60 cassettes per hour.

The blocks of hardened paraffin containing the embedded tissue samples are then ready to be sliced into extremely thin sections for placement on a microscope slide. The histotechnician mounts the embedded tissue block in a chuck on the microtome that is sized to accept the side of the block that has the embedded plastic cassette. The histotechnician can then begin slicing the paraffin block which has the tissue sample embedded opposite to the plastic cassette surface. This yields a ribbon of individual slices of the tissue embedded in the hardened paraffin. The action of the microtome causes the individual slices to stick together when done properly and, subsequently, these very thin ribbons of slices are floated into a water bath and a glass slide is carefully placed underneath the slice. The slice, with the thin sectioned tissue sample embedded therein, is then adhered to the top of the slide.

When the histotechnician has enough slides from the tissue sample, the slides are placed into an automatic staining machine. The staining machine goes through a series of infiltrating steps to stain the different tissue and cells of the slide different colors. This helps the pathologist identify different structures and makes it easier to find any abnormalities in the tissue. After the staining procedure is complete, the slides are cover slipped and prepared for the pathologist to place under a microscope for analysis.

Based on the summary of the procedure provided above, it will be appreciated that conventional tissue sample handling and processing is a very labor-intensive process involving several manual steps performed by a histotechnician. Thus, repetitive stress injuries such as carpal tunnel syndrome are prevalent. This is especially true with the tissue sample embedding process. These multiple manual operations and repeated tissue handling increase the likelihood of human error and, moreover, require highly trained and skilled histotechnicians to ensure that the tissue samples ultimately adhered to the slides for analysis by the pathologist are in an optimum condition and orientation to make accurate diagnoses.

U.S. Pat. Nos. 5,817,032 (the '032 patent) and 7,156,814, and U.S. Patent Application Publication Nos. 2005/0226770; 2005/0147538; and 2005/0084425 disclose various improvements to this area of technology, including new manners of holding tissue samples during the grossing in, embedding, and microtome or slicing procedures. The disclosures of U.S. Pat. No. 5,817,032 (the '032 patent) and U.S. Patent Application Publication Nos. 2005/0226770; 2005/0147538; and 2005/0084425 are hereby fully incorporated by reference herein. For example, the '032 patent relates to a tissue trapping and supporting device, which may be a cassette, and which may be successfully sectioned using a microtome. When such a cassette is used, the tissue sample is immobilized within the cassette and subjected to the process for replacing tissue fluids with paraffin. Then, the tissue sample and the cassette are sliced at the same time for later mounting on microscope slides. Because the tissue sample is never removed from the cassette from the time it is processed in the tissue processing machine to the time that it is cut or sliced with the microtome, a significant amount of handling time is saved. Moreover, the chance for human error or tissue loss is significantly reduced due to the elimination of separate tissue handling steps. The '032 patent and the above-incorporated published applications also generally disclose further improvements that help to automate the overall process and, in conjunction with the novel tissue supports (e.g., cassettes), can even further reduce the handling steps during the entire procedure and make the procedure more reliable.

In spite of the various advances made in this field, there is an increasing need for additional improvements related to increased production capability and more consistent quality of embedded tissue samples and resulting slices or ribbons of embedded tissue that will be subject to diagnosis. This can be especially important when handling smaller tissue sample sizes, although the improvements to be disclosed herein are applicable to all tissue sample sizes.

SUMMARY

In one general embodiment, a histologic tissue sample support is provided and may generally comprise a tissue support coupled with a resilient cellular material. The resilient cellular material is a three dimensional, microtome sectionable, deflectable structure that is an improvement upon the microtome sectionable, deflectable structures disclosed in the above-incorporated '032 patent discussed above. The tissue sample support device can more specifically include a tissue support formed of material which can be successfully sectioned in a microtome and is resistant to degradation from solvents and chemicals used to fix, process and stain tissue. The porosity of the resilient cellular material allows infiltration of the solvents and chemicals used to fix, process and stain tissue, and of embedding material used to embed the tissue while the tissue is retained by the resilient cellular material. The resilient cellular material has a thickness that is compressible and configured to engage and retain tissue in place during processing and embedding and is also capable of successful sectioning in the microtome after having its interstices or pores filled with liquefied embedding material which subsequently hardens.

The resilient cellular material may further comprise an open cell foam material, such as a foam including at least one of a polyether or a polyurethane. In addition, the open cell foam may be a fully reticulated foam. This helps ensure full infiltration of fluids used during processing and embedding procedures. Other synthetic and natural materials may be used such as polyesters, alginates, or other materials that may be infiltrated with the embedding material and successfully sectioned and a microtome without adverse effects on the resulting ribbon of tissue and embedding material.

The support may further include a tissue containment portion including a recess or interior area surrounded by at least one side wall and including a bottom wall. The recess or interior area may be configured to at least partially contain the resilient cellular material either during the manufacturing of the device or during insertion of the cellular material into the recess or interior area by the user in order to retain the tissue sample in place during processing and embedding procedures. The support can further comprise a cassette having a lid configured to be connected to the containment portion. In one embodiment, the resilient cellular material is coupled to the lid and is inserted at least partially into the recess upon connecting the lid to the containment portion.

The material forming the support may be at least translucent so as to be non-distracting during tissue analysis. For example, the support may be formed of any of the materials disclosed in the above incorporated patent and patent applications such as polymers including fluorinated polymers or fluoropolymers (e.g., PFA).

An assembly may be constructed with the support and a separate frame. In such an assembly, the tissue support is releasably retained on the frame and the frame is further configured for releasable securement within a microtome chuck. The frame can further include an interior and the tissue support may be sized to fit and move within the interior between at least a first position and a second position. The first position is used during processing of the tissue sample, and the second position is used to expose the tissue outward of the frame in a position for allowing the tissue sample to be sectioned in the microtome.

Various methods are disclosed or will be apparent based on a review of the disclosed embodiments and features. For example, a method for preparing one or more biopsy tissue samples for histological examination may comprise:

positioning a tissue sample in close proximity to a microtome sectionable support;

immobilizing the tissue sample on a the support by contacting the tissue sample with a microtome sectionable, resilient cellular material coupled to the tissue support;

subjecting the microtome sectionable support, resilient cellular material and the tissue sample to a process that replaces fluid in the tissue sample with a hardenable material;

embedding the microtome sectionable support, resilient cellular material and the tissue sample in an embedding material;

hardening the embedding material into a block; and slicing the block with a microtome into thin slices of the embedding material, the microtome sectionable support, the resilient cellular material and the tissue sample.

The hardenable material and the embedding material may be the same material, such as a wax (e.g., paraffin). The support may further comprise a bottom portion configured to hold the tissue sample and a lid holding the resilient cellular material. The step of immobilizing the tissue sample can further comprise closing the lid on top of the tissue sample to trap the tissue sample between the resilient cellular material and the bottom portion. The bottom portion can include an interior space surrounded by at least one side wall and the positioning and immobilizing steps and can further comprise placing the tissue sample within the interior space, and inserting the resilient cellular material at least partially into the interior space and into contact with the tissue sample. The resilient cellular material may deform during the immobilizing step to create a three dimensional space that receives the tissue sample. This can help immobilize the tissue sample in a desired form flat against the bottom of the support or cassette. The force of the resilient cellular material against the tissue should be enough to immobilize and/or flatten the tissue but not enough to induce artifacts in the sample. The microtome sectionable support may be coupled to a frame prior to being subjected to the process for replacing fluid in the tissue sample with the hardenable material. The method can then further comprise securing the frame in the microtome prior to slicing the block. Prior to embedding the microtome sectionable support, resilient cellular material and the tissue sample in the embedding material, the microtome sectionable support may be moved from a first position within the frame to a second position in which the support, resilient cellular material and tissue sample are exposed for simultaneous sectioning in the microtome.

Various additional details, features, advantages and aspects of the invention will become more readily apparent to those of ordinary skill in the art on review of the following illustrative, more detailed description.

DETAILED DESCRIPTION

Figure 1:
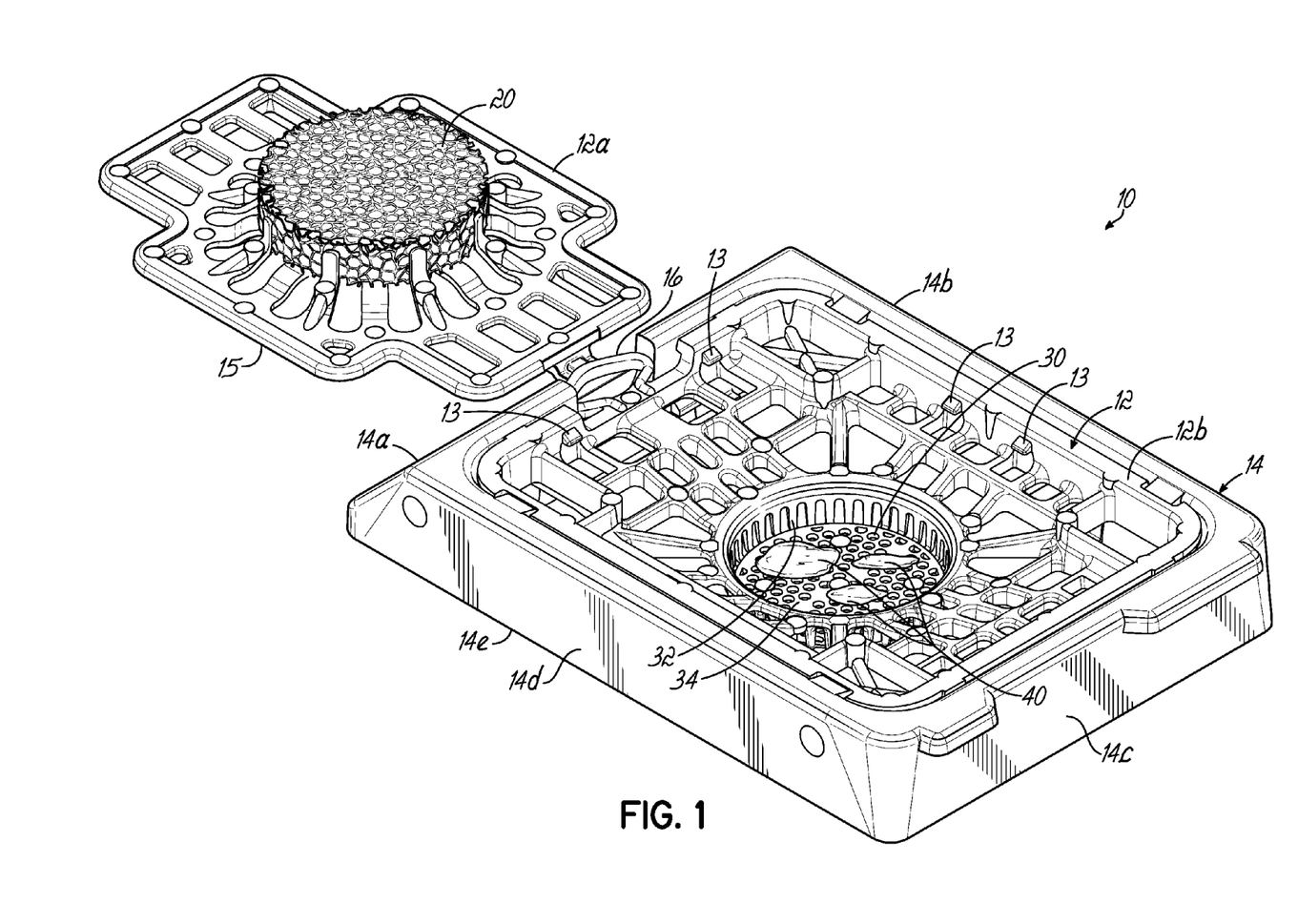
FIG. 1 is a perspective view of an assembly comprised of a microtome sectionable tissue cassette received within a frame, with the lid of the cassette shown in an open position.
Figure 2:
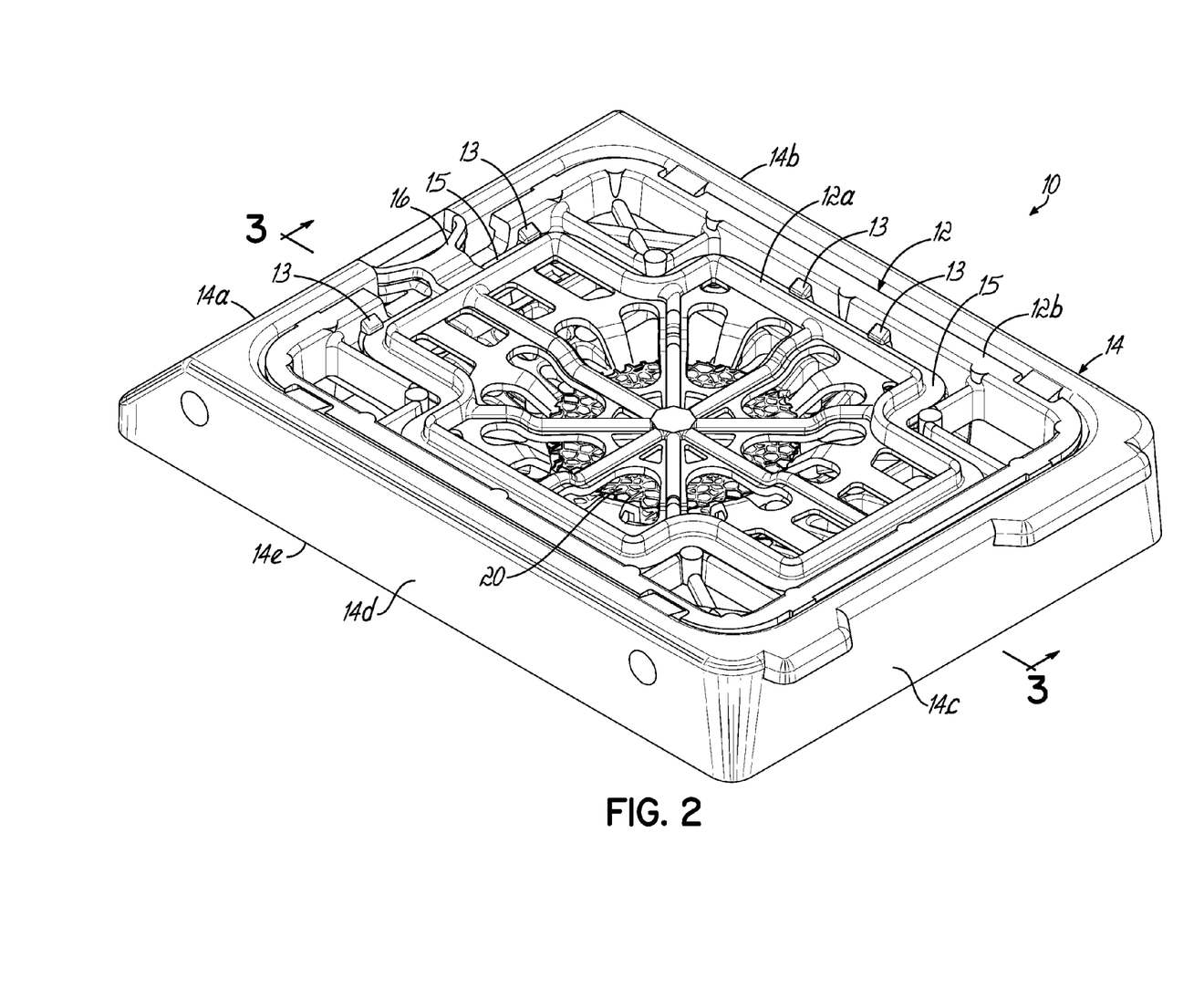
FIG. 2 is a perspective view similar to FIG. 1, but illustrating the lid of the cassette in a closed position.
Figure 3:
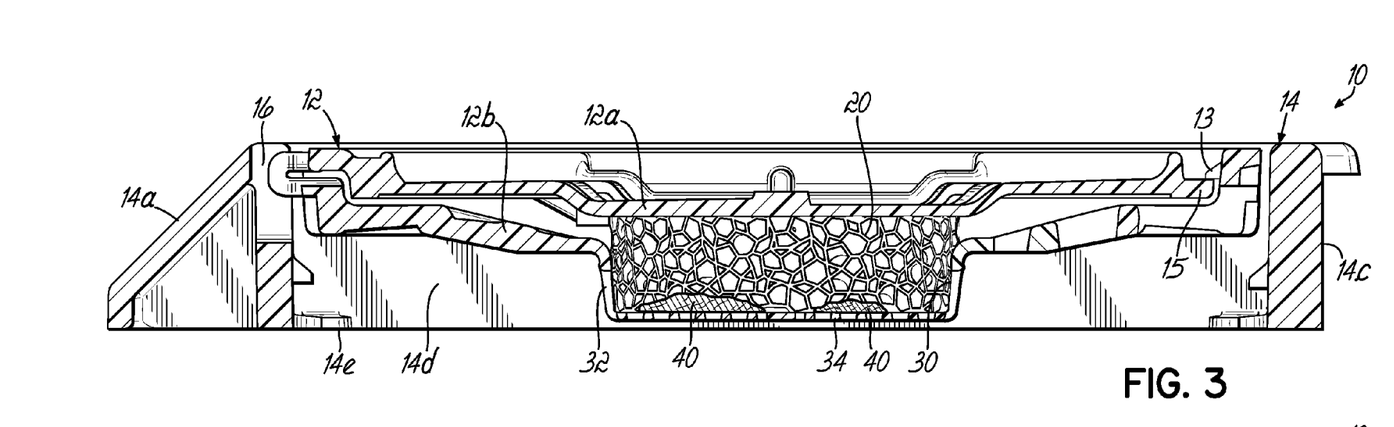
FIG. 3 is a cross sectional view generally taken along line 3-3 of FIG. 2.

FIGS. 1 and 2 generally illustrate an assembly 10 comprised of a tissue sample cassette 12 carried within a frame 14. The connection of the tissue cassette 12 to the frame 14 may be accomplished in many different manners, such as any of the manners described in the above-incorporated patent and patent applications. It will be also be appreciated that the cassette 12 may be configured in any suitable manner as a tissue support and the frame 14 may be configured in any suitable manner. Any of the configurations, features, characteristics and materials disclosed for the tissue supports (e.g., cassettes) and frames in the above-incorporated patent and patent applications may be employed for cassette 12 and frame 14. In the embodiment shown, the cassette 12 is porous and is releasably retained in the frame 14 and the frame 14 is further configured to be releasably secured within a microtome chuck (not shown). The frame 14 generally includes an interior defined between surrounding outer walls 14a, 14b, 14c, 14d and the cassette 12 is sized and configured to frictionally or "snap" fit and move within the interior between at least first and second positions, again, as generally discussed in the above-incorporated patent and patent applications and for the same purposes. The first position is shown in FIG. 3, while the second position is a position (not shown) in which the lower portion of the cassette 12 is exposed below the bottom of the frame 14, as viewed in FIG. 3, for allowing the cassette 12 and tissue sample to be sectioned in a microtome while the frame 14 is held in the microtome chuck. The general procedure for processing, embedding, and sectioning is discussed in the above-incorporated patent and patent applications. The cassette may be formed from perfluoroalkoxyethylene (PFA) in accordance with the above-incorporated patents and patent applications.

A lid 12a of the cassette 12 may be coupled to a body 12b of the cassette 12 by a hinge 16. The lid 12a may also snap fit into a closed position as shown in FIG. 2 through engagement of fingers or projecting connectors 13 on the cassette body 12b with an outer flange 15 of the lid 12a on each of the four sides of the lid 12a. The lid 12a carries a resilient cellular material 20 which may, for example, be an open cell foam material, such as a foam including at least one of a polyether or a polyurethane and which may be a fully reticulated foam. Here, "fully reticulated" means that at least substantially all cells of the foam are open. As shown in FIG. 1, one or more tissue samples may be placed in a porous tissue containment portion 30 that may define a recess or interior area surrounded by at least one sidewall 32 and including a bottom wall 34. Although a circular recess is shown, it will be appreciated that any other shape may be used instead.

Figure 5:
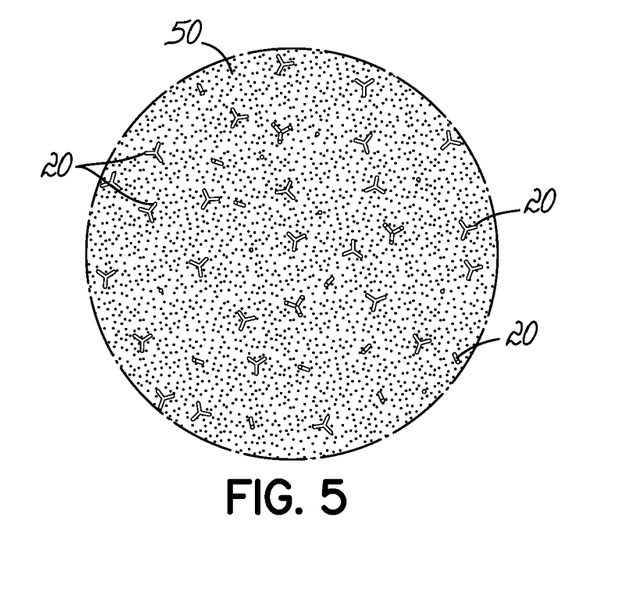
FIG. 5 is a cross sectional view taken generally along line 5-5 of FIG. 4.
Figure 6:
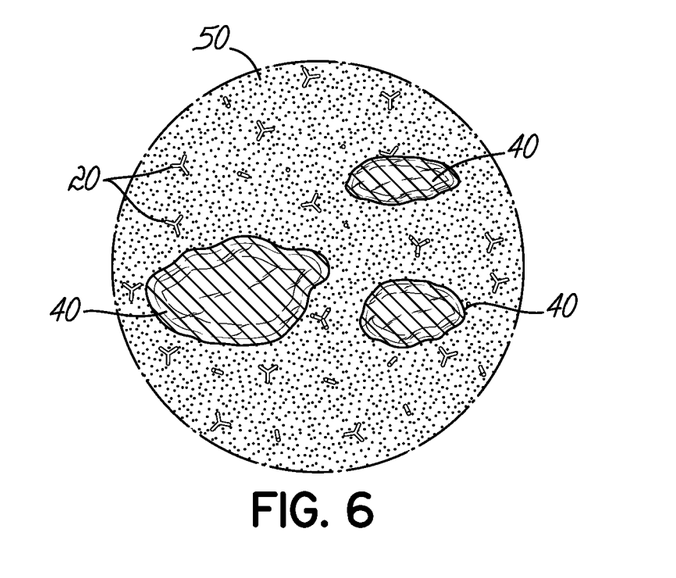
FIG. 6 is a cross sectional view taken generally along line 6-6 of FIG. 4.
Figure 7:
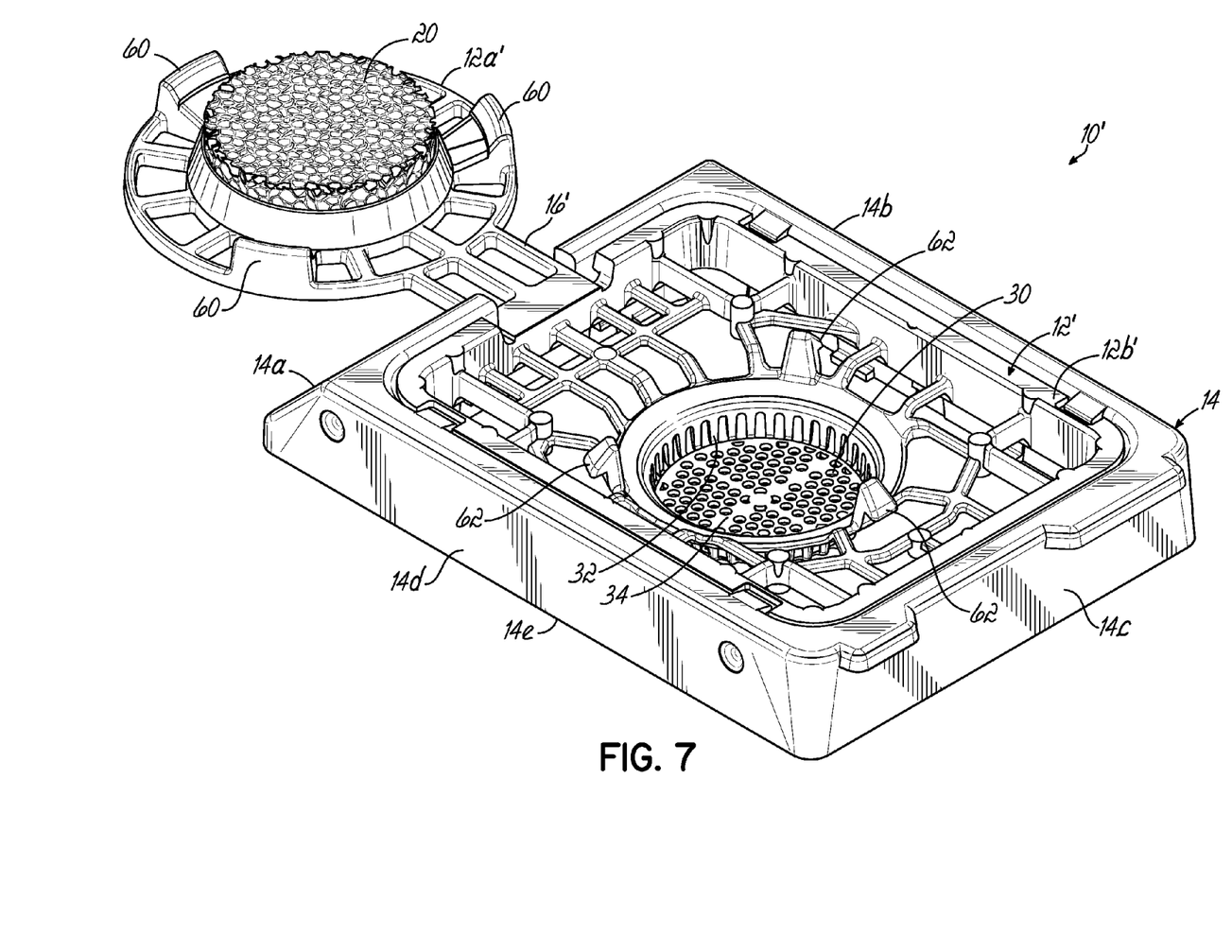
FIG. 7 is a perspective view of an assembly comprised of a microtome sectionable tissue cassette constructed according to another embodiment, and received within a frame, with the lid of the cassette shown in an open position.

As further shown in FIG. 3, when the lid 12a is closed, the foam material 20 will press against the tissue samples 40 and deform three dimensionally around the tissue samples 40 creating three dimensional spaces around each tissue sample 40 and essentially immobilizing each tissue sample 40 during the tissue processing and embedding procedures. This also ensures that the tissue samples 40 are held flat against the bottom wall 34 of the tissue cassette 12 such that when microtome slices are made, complete and continuous sections of the tissue sample 40 may be formed generally as shown in FIG. 5. One specific type of foam structure suitable for the resilient cellular material 20 has a pore size of 50-60 ppi (pores per inch), with each pore having a diameter of between about 0.017 inch and 0.20 inch. The foam structure is fully reticulated with a compression force deflection at 20% deflection of 0.55 lbs./in$^2$ and a density of 1.4 lbs./ft$^3$. The foam material may be obtained from Crest Foam of Moonachie, N.J. under the name T-50. This is a polyether/polyurethane foam and operates well with a thickness of 0.06 inch to 0.10 inch with a 0.075 inch thickness being a practical manufacturing example. The foam should be constructed so as to shed or release processing fluid after each reagent cycle of a tissue processing machine. If the foam is too dense or too thick, or not fully reticulated, the reagents can become cross contaminated or the tissue may not be fully infiltrated with the fluids because each fluid bath must fully clear and exchange from one fluid bath to the next.

In use, one or more tissue samples 40 are placed within the interior space or recess and, specifically, on the bottom wall 34 as shown in FIG. 1. The cassette lid 12a is then closed and snapped into place such that the resilient cellular material (e.g., foam) 20 bears against and traps the tissue samples 40 against the bottom wall 34 as shown in FIG. 3. At this point, the assembly 10 with the trapped tissue samples 40 may be subjected to a conventional tissue processing operation that uses vacuum, heat and chemicals to remove the interstitial fluids within the tissue and replace those fluids with a hardenable material, such as molten paraffin. As mentioned above, during these processing steps, the porous nature of the foam or other resilient cellular material 20 allows the fluids to reach and fully infiltrate into the tissue samples 40. In addition, the foam 20 traps the tissue samples 40 flat against the bottom wall 34 without leaving artifacts or markings on the tissue that might interfere with subsequent analysis under a microscope. It will be appreciated that different types of resilient cellular materials may be chosen based, for example, on the type of tissue to be processed and analyzed. For example, small mucosal tissue samples may be held and processed with success using the T-50 foam discussed above, while other types of tissue, such as fatty tissue, may be better served by another type of resilient cellular material.

Figure 4:
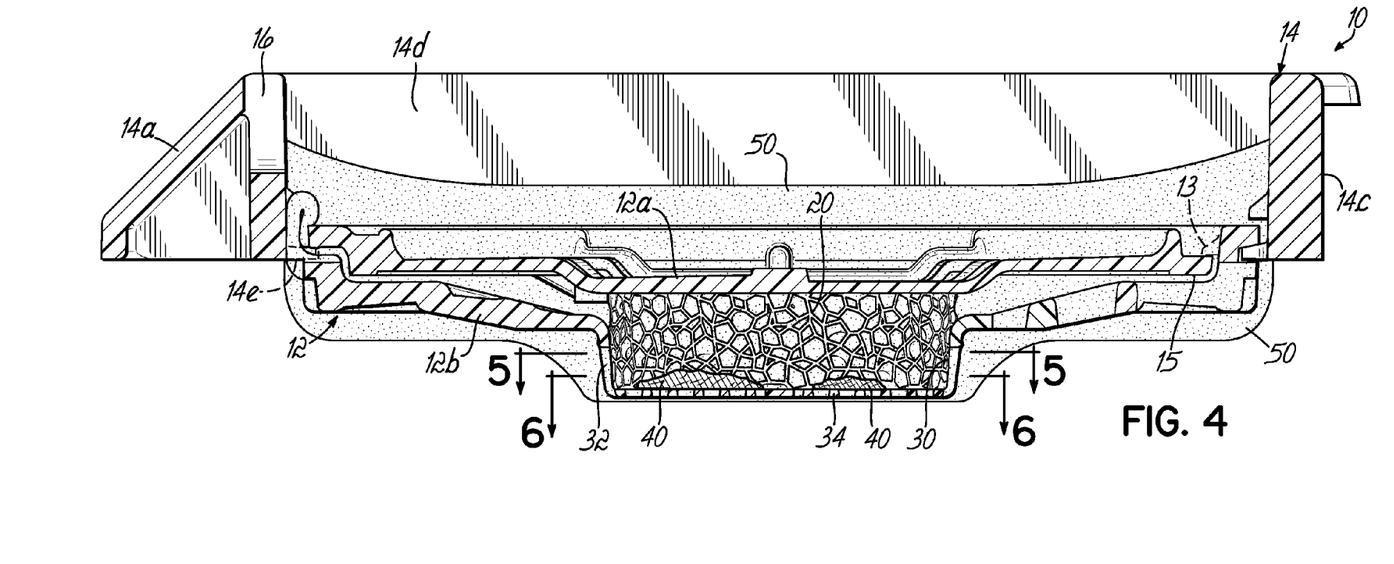
FIG. 4 is a cross sectional view similar to FIG. 3, but showing the cassette/frame assembly embedded in paraffin and with the cassette in a second, lower position within the frame for sectioning.

It will also be appreciated that the processing steps may take place before assembling the tissue cassette 12 with the frame 14. After the tissue processing is complete, the tissue cassette 12 may be moved to a second position as shown in FIG. 4 exposing the containment portion 30 below the bottom surface 14e of the frame 14. The cassette 12 and frame 14 are then placed into a suitable mold (not shown) and embedded in paraffin 50, such that the entire assembly including the lower exposed containment portion 30 are embedded within a hardened block of paraffin wax 50. The mold may generally follow the contour of the bottom of the cassette 12, although the portion of the mold surrounding the containment portion 30 is preferably square as opposed to round. This assists with the subsequent production of ribbon slices. This portion of the procedure may therefore be similar to that disclosed in the above-incorporated patent and patent applications. As discussed therein, the frame 14 is then used as a fixture for mounting the embedded assembly 10 in a microtome chuck and the necessary number of slices are taken of the exposed underside until enough sections, similar to those shown in FIG. 5, are taken and appropriately mounted on a microscope slide, stained and cover slipped.

FIGS. 7-10 illustrate an alternative embodiment. In this embodiment, the cassette is constructed with a somewhat different design than the first embodiment as will be apparent from a review of the figures, as well as the description below. Like reference numerals in FIGS. 1-10 refer to like structure and, therefore, additional description with respect to FIGS. 7-10 is not necessary. Like reference numerals in FIGS. 7-10 having prime marks (') refer to analogous elements as shown and described in connection with FIGS. 1-6 but having differences that are either apparent by reviewing the drawings themselves or by a combination of reviewing the drawings and the additional description contained below.

Figure 8:
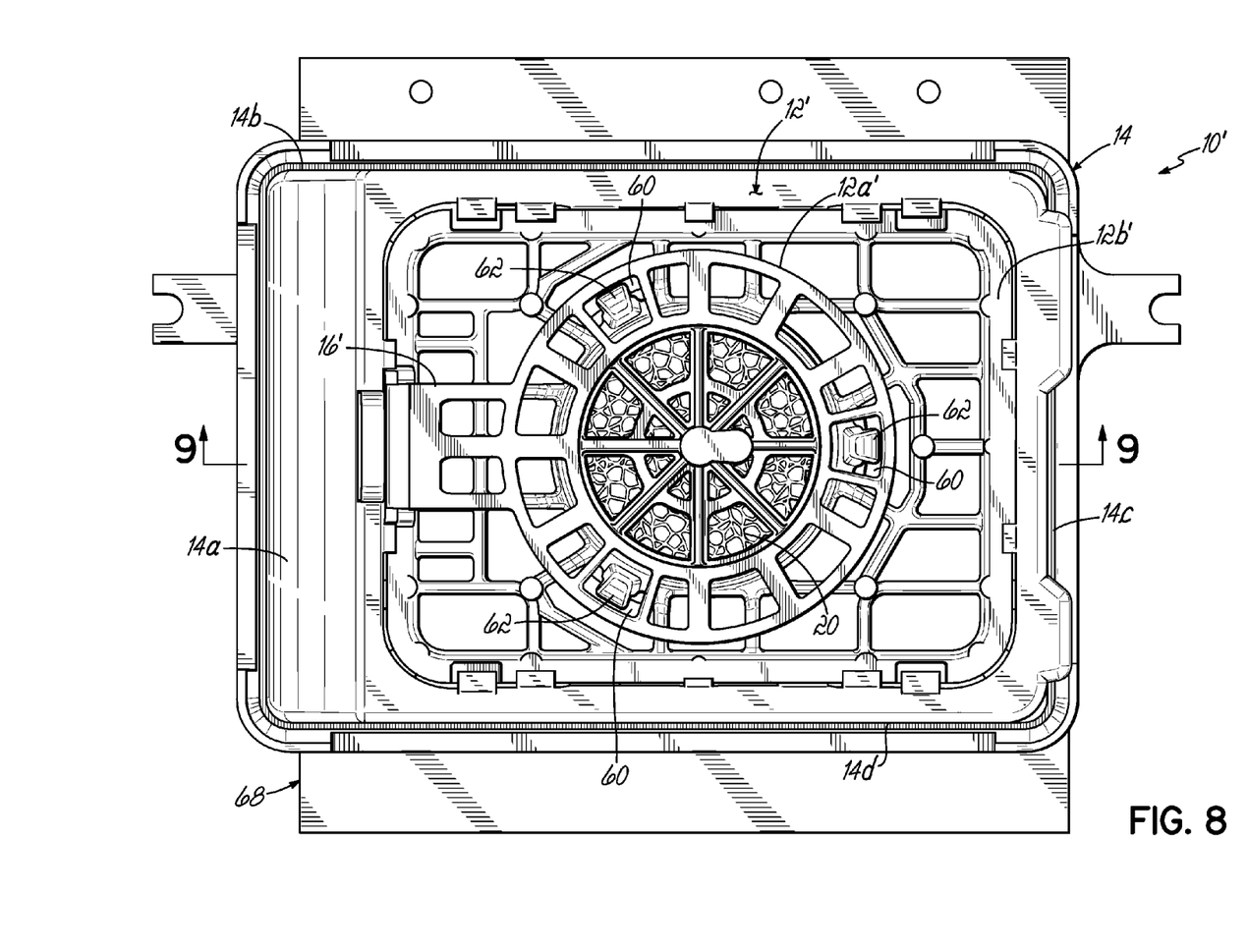
FIG. 8 is a top view of the assembly shown in FIG. 7, but with the lid in a closed position, and the assembly in a mold.
Figure 9:
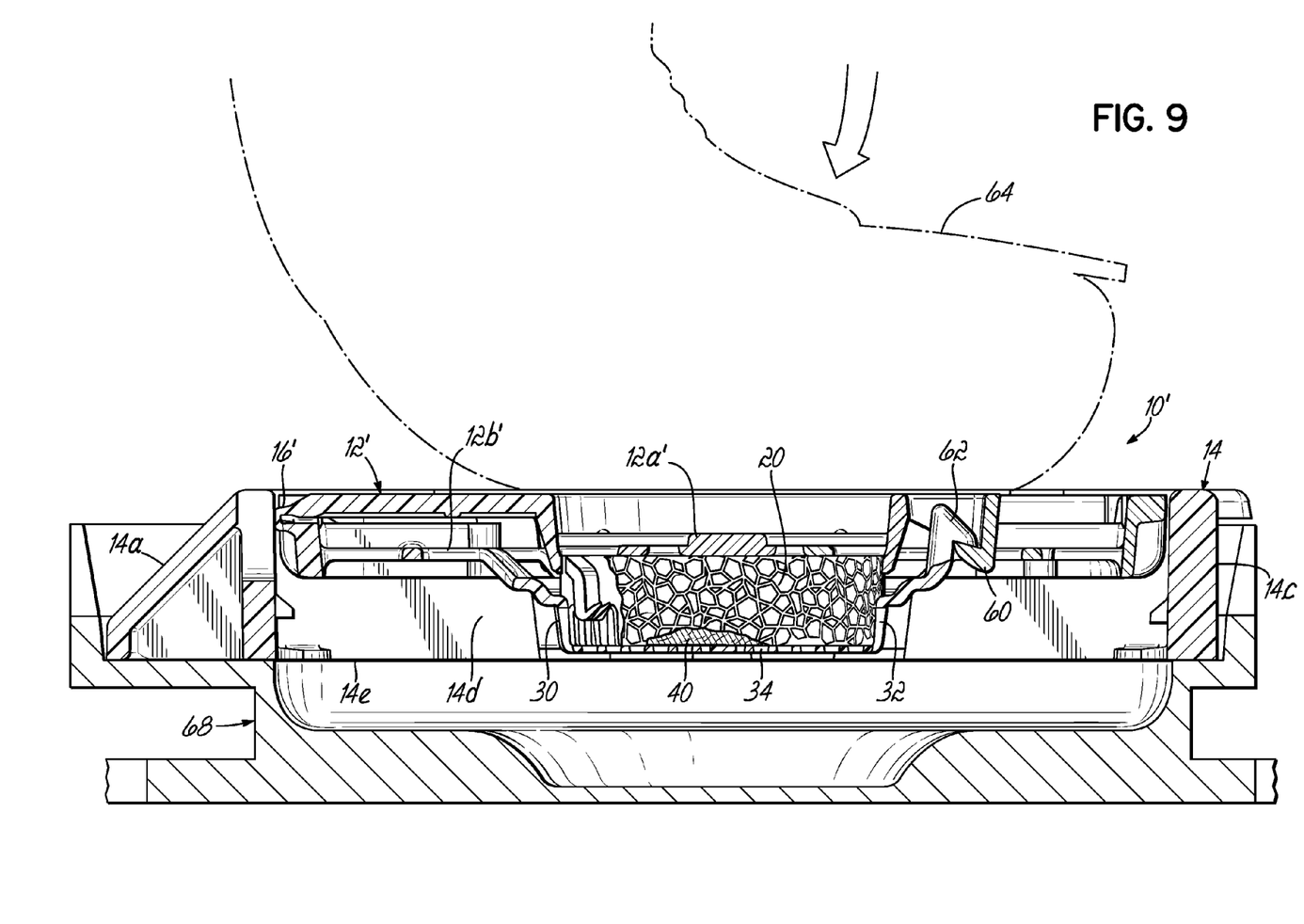
FIG. 9 is a cross sectional view taken along line 9-9 of FIG. 8 and schematically illustrating the lid being depressed into a closed position.
Figure 10:
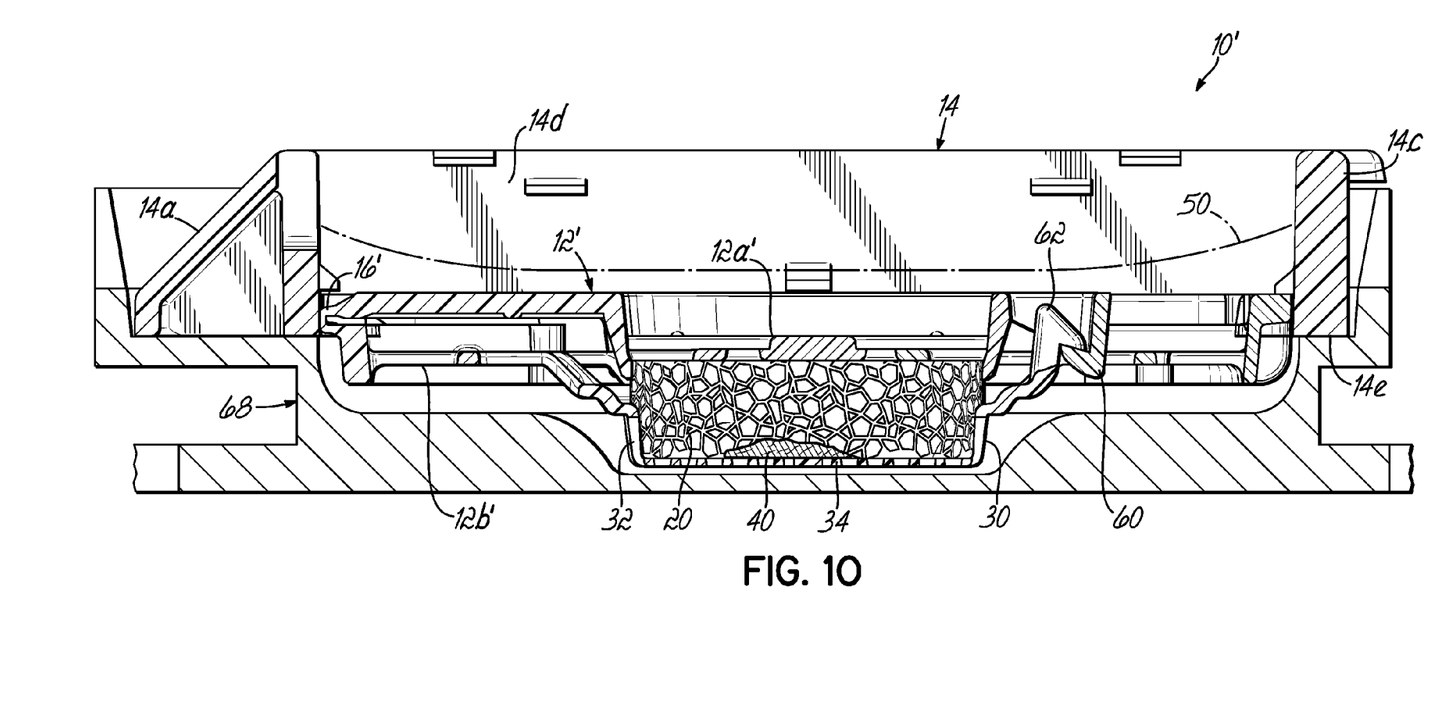
FIG. 10 is a cross sectional view similar to FIG. 9, but illustrating the cassette in a second, lower position within the frame such that a lower portion of the cassette extends into the mold.

The primary difference between assembly 10 and assembly 10' is with respect to the lids 12a, 12a' and the manner that the lids 12a, 12a' connect with the bodies 12b, 12b' of the cassettes 12, 12'. In the first embodiment, the lid 12a is held down to the body 12b by a series of snap fit connectors 13 on each of the four sides of the cassette body 12b. These connectors 13 engage an outer flange section 15 of the lid 12a. Thus, the user typically would use his or her finger to depress each of the four sides of the cassette lid 12a downward to engage each of the sets of snap fit connectors 13. The cassette 12' shown in FIGS. 7-10 instead uses a circular lid 12a' having three connecting elements 60 spaced apart by 120°. Elements 60 connect in a snap fit manner with connectors 62 on the cassette body 12b' when the lid 12a' is folded over as shown in FIGS. 8 and 9. As further illustrated in FIG. 9, the lid 12a' may be closed and locked in a snap fit manner utilizing the three mating connectors 60, 62 by depressing the lid 12a' with a single finger 64 of the user. As previously discussed, the cassette 12' may be depressed entirely as a unit from the upper position in the frame 14, illustrated in FIG. 9, to the lower position shown in FIG. 10. This extends the porous tissue containment portion 30 into the mold 68. The mold may then be filled with embedding material such as paraffin 50. A structure is thereby formed as previously described in connection with FIG. 4. It will further be appreciated that the basic perforated design of the cassette 12' is changed relative to the perforated design of the cassette 12 illustrated in FIGS. 1-6. Essentially, the design of the molded cassette 12' illustrated in FIGS. 7-10 reduces the amount of PFA material necessary to form the cassette 12'. All other structural and functional aspects and uses of assembly 10' are as described in connection with assembly 10 of the first embodiment.

While the present invention has been illustrated by a description of various illustrative embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or any combinations depending on the needs and preferences of the user. However, the invention itself should only be defined by the appended claims.

What is claimed is:

1. A method for preparing one or more biopsy tissue samples for histological examination, comprising:
   positioning a tissue sample in close proximity to a microtome sectionable support;
   immobilizing the tissue sample against the support by contacting the tissue sample with a microtome sectionable, open cell fully reticulated foam material;
   subjecting the microtome sectionable support, the open cell fully reticulated foam material and the tissue sample to a process that prepares the tissue sample for embedding;
   embedding the microtome sectionable support, the open cell fully reticulated foam material and the tissue sample in an embedding material;
   hardening the embedding material into a block; and
   slicing the block with a microtome into thin slices of the hardened embedding material, the microtome sectionable support, the open cell fully reticulated foam material and the tissue sample.

2. The method of claim 1, wherein the embedding material is wax.

3. The method of claim 1, wherein the microtome sectionable support further comprises a bottom portion configured to hold the tissue sample and a lid holding the open cell fully reticulated foam material, and the step of immobilizing the tissue sample further comprises:
   closing the lid on top of the tissue sample to trap the tissue sample between the open cell fully reticulated foam material and the bottom portion.

4. The method of claim 3, wherein the bottom portion includes an interior space surrounded by at least one side wall and the positioning and immobilizing steps further comprise:
   placing the tissue sample within the interior space; and
   inserting the open cell fully reticulated foam material at least partially into the interior space and into contact with the tissue sample.

5. The method of claim 3, wherein the open cell fully reticulated foam material deforms during the immobilizing step to create a three dimensional space that conforms to the tissue sample.

6. The method of claim 1, wherein the microtome sectionable support is coupled to a frame prior to the process for preparing the tissue sample for embedding, and the method further comprises securing the frame in the microtome prior to slicing the block.

7. The method of claim 6, wherein prior to embedding the microtome sectionable support, open cell fully reticulated foam material and the tissue sample in the embedding material, the microtome sectionable support is moved from a first position within the frame to a second position in which the support, open cell fully reticulated foam material and tissue sample are exposed for simultaneous sectioning in the microtome.

8. The method of claim 1, wherein the process for preparing the tissue sample for embedding further comprises:

replacing fluid in the tissue sample with a hardenable material.

\* \* \* \* \*